United States Patent [19]

Coates et al.

[11] 4,053,601

[45] Oct. 11, 1977

[54] 3-SUBSTITUTED-PHENYL-6-HYDRAZINE PYRIDAZINES

[75] Inventors: William John Coates, Welwyn Garden City; Anthony Maitland Roe, Hatfield; Robert Antony Slater, Letchworth; Edwin Michael Taylor, Welwyn, all of England

[73] Assignee: Smith Kline & French Laboratories Limited, Welwyn Garden City, England

[21] Appl. No.: 583,379

[22] Filed: June 3, 1975

[30] Foreign Application Priority Data

June 18, 1974 United Kingdom ............... 26864/74

[51] Int. Cl.$^2$ .................... A61K 31/50; C07D 237/20
[52] U.S. Cl. ................. 424/250; 260/250 A; 260/343.3 R; 260/465 F; 260/473 R; 560/23; 560/22; 560/43; 560/53
[58] Field of Search .................... 260/250 A; 424/250

[56] References Cited

U.S. PATENT DOCUMENTS

| | | | |
|---|---|---|---|
| 3,769,278 | 10/1973 | Pifferi | 424/250 |
| 3,818,097 | 6/1974 | Black et al. | 424/273 |
| 3,881,015 | 4/1975 | Black et al. | 424/273 |
| 3,975,530 | 8/1976 | Durant | 424/270 |

OTHER PUBLICATIONS

Gross et al., Chem. Abs., 46, 11261g (1952).

*Primary Examiner*—Donald G. Daus
*Assistant Examiner*—Mark L. Berch
*Attorney, Agent, or Firm*—Joan S. Keps; Richard D. Foggio; William H. Edgerton

[57] ABSTRACT

The compounds are 3-((3-substituted amino-2-hydroxy-propoxy)-phenyl)-6-hydrazino pyridazines which have $\beta$-adrenergic blocking and vasodilator activity.

25 Claims, No Drawings

3-SUBSTITUTED-PHENYL-6-HYDRAZINE PYRIDAZINES

This invention relates to pharmacologically active compounds and in particular to certain substituted phenyl hydrazinopyridazines which have β-adrenergic blocking and vasodilator activity. This invention also relates to pharmaceutical compositions comprising said compounds and to methods of treatment employing their use.

The compounds of the present invention may be represented by the following Formula I:

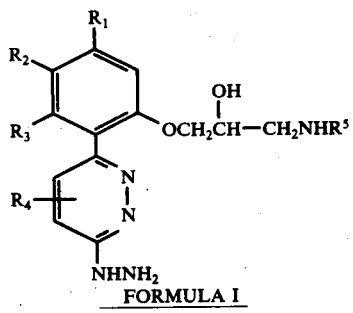

FORMULA I wherein two of the groups $R_1$, $R_2$ and $R_3$ are hydrogen and the third group is hydrogen, lower alkyl, fluoro, chloro, bromo, trifluoromethyl, hydroxy, lower alkoxy, lower alkenyloxy, lower alkoxycarbonyl, cyano, —$CONH_2$, —$CH_2CONH_2$, nitro, amino, lower alkanoylamino, lower alkylamino or di(lower alkyl)amino: $R_4$ is hydrogen or methyl; $R^5$ is isopropyl, tertiary butyl or phenylethyl. The invention also includes pharmaceutically acceptable acid addition salts of the compounds of Formula I.

Throughout the specification and claims, by the terms 'lower alkyl', 'lower alkoxy', 'lower alkenyloxy' and 'lower alkanoyl' we mean alkyl, alkoxy, alkenyloxy and alkanoyl groups containing a chain of no more than four carbon atoms, which chain may, where possible, be branched.

In a preferred group, $R_1$, $R_2$ and $R_3$ are all hydrogen, or one of $R_1$, $R_2$ and $R_3$ is methyl, fluoro, chloro, methoxy or cyano. Particularly preferably $R_3$ is hydrogen.

In another preferred group $R_3$ is hydrogen and either $R_1$ or $R_2$ is trifluoromethyl, allyloxy, —$CH_2CONH_2$ or acetamido, particularly preferably —$CH_2CONH_2$ or acetamido. Preferably $R_4$ is hydrogen.

Preferably $R^5$ is isopropyl or tertiary butyl.

Examples of particularly preferred compounds which fall within the scope of the present invention are:

3-[2-(3-t-butylamino-2-hydroxypropoxy)phenyl]-6-hydrazinopyridazine

3-[2-(3-t-butylamino-2-hydroxypropoxy)-4-methylphenyl]-6-hydrazinopyridazine

3-[2-(3-t-butylamino-2-hydroxypropoxy)-4-methoxyphenyl]-6-hydrazinopyridazine

3-[2-(3-t-butylamino-2-hydroxypropoxy)-6-fluorophenyl]-6-hydrazinopyridazine

3-[4-acetamido-2-(3-t-butylamino-2-hydroxypropoxy)phenyl]-6-hydrazinopyridazine.

The compounds of this invention exist as optical isomers and the S-absolute configuration is preferred. Racemic mixtures of the compounds of Formula I can be resolved by conventional methods, such as recrystallisation of salts formed with optically active acids, but preferably the intermediates of Formula 5 and Formula 14 are resolved before conversion into hydrazinopyridazines.

The compounds of Formula I may be prepared by the processes outlined in Scheme 1. In the schemes $R^1$, $R^2$ and $R^3$ have the same significance as in Formula I or they may also be protected derivatives thereof or precursors thereof.

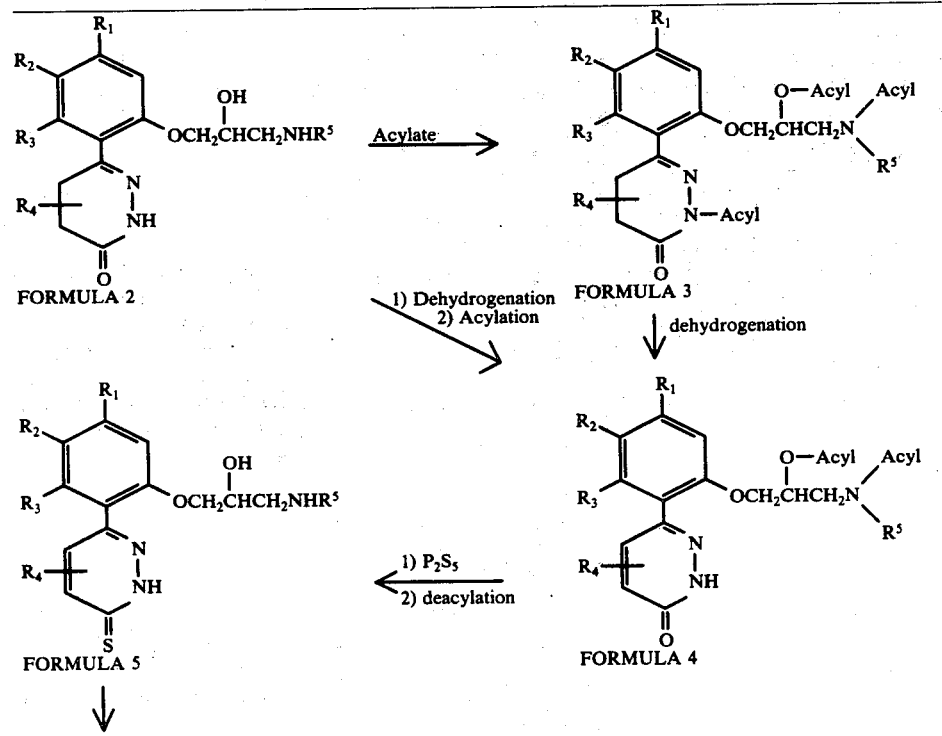

SCHEME 1

-continued
SCHEME 1

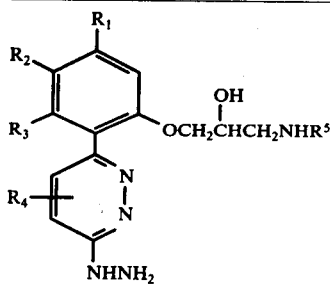

FORMULA 1

Acylation of a phenyl dihydropyridazinone of Formula 2, wherein $R_1$, $R_2$, $R_3$, $R_4$ and $R^5$ have the same significance as in Formula I, gives a compound of Formula 3, wherein the hydroxy and amino groups of the side chain are protected. A suitable acyl group is the acetyl group which may be introduced by reaction of a compound of Formula 2 with acetic anhydride in the presence of a suitable base, e.g., pyridine or potassium acetate. Acetylation of the dihydropyridazinone ring also occurs, and this acetyl group is removed during subsequent bromination. Another suitable acyl group is the benzyloxycarbonyl group which may be introduced by treating a compound of Formula 2 with benzyl chloroformate under basic conditions. The triacylated compound of Formula 3 is dehydrogenated to gave a phenylpyridazinone of Formula 4.

In many cases bromine in acetic acid is a suitable reagent for this dehydrogenation, and when the acyl group is acetyl it is preferred that the compound of Formula 3 is not isolated before the treatment with bromine. In cases where the use of bromine is inappropriate, e.g., where the compound of Formula 2 is susceptible to nuclear bromination (i.e., when $R_1$, $R_2$ or $R_3$ is a group such as hydroxy or amino), and when $R_1$, $R_2$ or $R_3$ is sensitive to bromine or hydrogen bromide (e.g. allyloxy), dehydrogenation of a compound of Formula 2 can be achieved by the use of sodium 3-nitrobenzene sulphonate, chloranil or other similar dehydrogenating agents, and is followed by acylation to give a compound of Formula 4. Treatment of the phenylpyridazinone of Formula 4 with phosphorus pentasulphide in pyridine gives the corresponding thione (which may be obtained in mixture with the corresponding N-thioacylaminopropyl derivative) which is deacylated under suitable conditions to give the thione of Formula 5. The acetyl group may conveniently be removed using sodium hydroxide in methanol. Treatment of the thione of Formula 5 with hydrazine gives the required compound of Formula I.

The compounds of Formula 5 are referred to as thiones and are drawn as such, but these compounds may also exist in a tautomeric mercaptopyridazine form. Similarly the dihydropyridazinones of Formula 2 may exist as a tautomeric mixture with the corresponding hydroxypyridazines. The intermediate phenyl dihydropyridazinones of Formula 2 may be prepared according to a reaction sequence shown in Scheme 2, wherein $R_1$, $R_2$, $R_3$, $R_4$ and $R^5$ have the same significance as in Formula I and one of $R^6$ and $R^7$ may be methyl and $R^8$ is hydroxy, amino or any other suitable group such as lower alkoxy or lower alkylamino, which can be displaced with hydrazine.

Many of the phenyldihydropyridazinones of Formula 2 are described in our co-pending U.S. Pat. application Ser. No. 531,597, now U.S. Pat. No. 3,946,353.

The compounds of Formula 6 may be produced from the corresponding compounds of Formua 8:

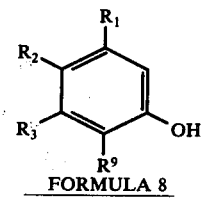

FORMULA 8 wherein $R_1$, $R_2$ and $R_3$ have the same significance as in Formula I and $R^9$ is hydrogen or bromine or —COCH$_2$R$_4$. When $R^9$ is hydrogen, reaction with succinic anhydride and a Lewis acid such as aluminum trichloride may be used. When $R^9$ is bromine, formation of a Grignard reagent with magnesium and subsequent reaction of this with, for example, N-methylsuccinimide provides a useful method, the hydroxyl group being protected during this reaction for example by benzylation.

SCHEME 2
(X represents Chlorine or Bromine)

SCHEME 2 -continued

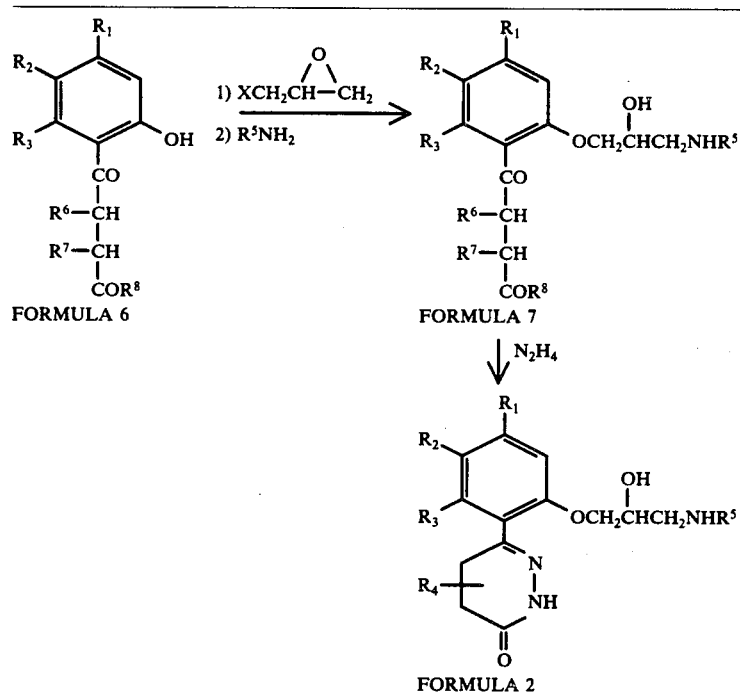

In each case of course the succinic anhydride or N-methylsuccinimide may be substituted with a methyl group to give the appropriate compounds of Formula 6 wherein either $R^6$ or $R^7$ is methyl. When $R^9$ is —COCH$_2$R$_4$, the phenol of Formula 8 is treated with formaldehyde and a di-(lower alkyl) amine to give a compound of Formula 9 wherein $R^{10}$ is lower alkyl or $(R^{10})_2$ is a polymethylene chain which forms a heterocyclic ring with the nitrogen atom shown. The compounds of Formula 9 may be alkylated to give the corresponding quaternary derivatives. The compounds of Formula 9 and the corresponding quarternary derivatives may be treated wth an inorganic cyanide to give a cyanide of Formula 10. The phenol group may be protected, for example as the acetate ester, during these processes.

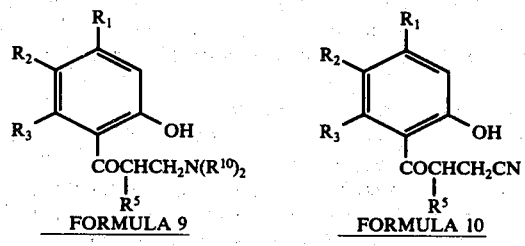

The compounds of Formula 2 may readily be obtained from the cyanides of Formula 10 e.g., by hydrolysis of the latter to the corresponding amides or carboxylic acids.

The compounds of Formula 6 are successively treated with epichlorohydrin or epibromohydrin, an amine $R^5NH_2$, and hydrazine to give the phenyldihydropyridazinones of Formula 2. Alernatively, the phenyldihydropyridazinones of Formula 2 may be prepared by first treating the compounds of Formula 6 to give the dihydropyridazinones of Formula 9 and then successively treating these compunds with epichlorohydrin or epibromohydrin, and then an amine $R^5NH_2$, as shown in Scheme 3. With the latter route alkylation of the dihydropyridazinone ring may occur.

SCHEME 3

(X represents Chlorine or Bromine)

SCHEME 3

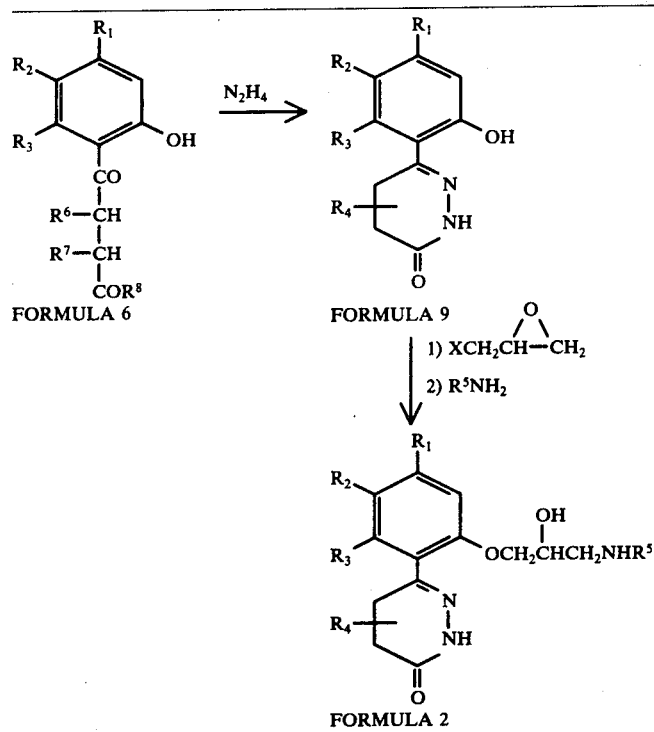

An alternative series of reactions is possible, wherein the various reactive groupings present in the compounds of our invention may be introduced at different stages from those illustrated in Scheme 1. One series, illustrated as Scheme 4, starts with the compound of Formula 11 and the additional double bond is first introduced into the 4,5-position of the pyridazinone ring by dehydrogenation under conditions mentioned above as being suitable for the dehydrogenation of the compounds of Formula 3. The phenolic group is then protected with a suitable protecting group, such as the ethoxycarbonyl group which may be introduced using ethyl chloroformate. The 3-oxo substituent of the pyridazine ring is converted into a 3-hydrazino group by treatment with phosphoryl chloride or phosphorus pentasulphide, removal of the phenolic protecting group and treatment of the produce with hydrazine or an alkoxide or phenoxide followed by hydrazine. For example, the ethoxycarbonyl protecting group may be removed under mild basic conditions. The hydrazino group is then protected by reacting it with an alkoxycarbonyl halide, a ketone or an aldehyde, and the 3-alkylamino-2-hydroxy-1-propoxy side chain is introduced by successive reaction with epichlorohydrin or epibromohydrin and an amine $R^5NH_2$. Removal of the protecting group on the hydrazino group (e.g., with acid) finally yields the required compounds of Formula I.

In all series of reactions described the hydrazino group may be introduced by reaction with hydrazine or a protected derivative thereof, such as t-butyl carbazate or a hydrazone of an aldehyde or ketone.

SCHEME 4

(X represents Cl or Br)

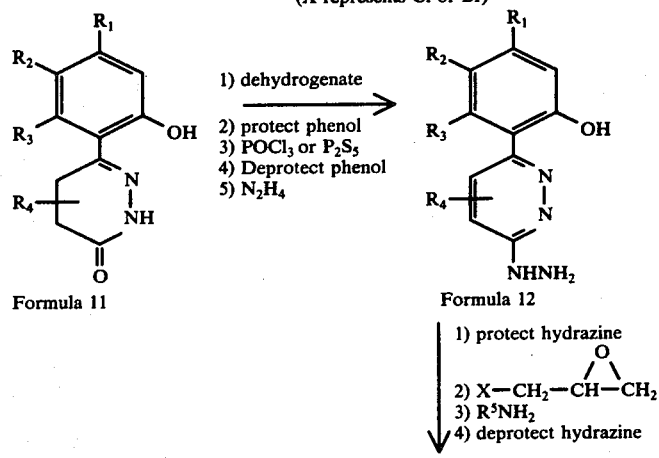

-continued
SCHEME 4

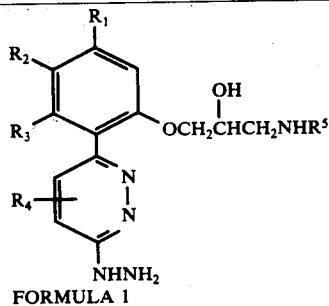
FORMULA 1

An alternative method for the preparation of compounds of Formula 1 which is particularly suitable when the phenylchloropyridazines of Formula 13 are easily accessible is outlined in Scheme 5. A phenylchloropyridazine of Formula 13 is successively treated with epichlorohydrin or epibromohydrin, and an amine $R^5NH_2$ to give a compound of Formula 14. The compounds of Formula 14 may be converted into the required compounds of Formula 1 directly by reaction with hydrazine, or by displacement of the chlorine with an alkoxide, e.g., methoxide, or phenoxide, and then displacement of this alkoxy or phenoxy group with hydrazine.

One method for the preparation of phenylchloropyridazines of Formula 13 is outlined in Scheme 6. Preferably a para-substituted phenol is treated with a mucohalic acid and an appropriate catalyst such as zinc chloride, polyphosphoric acid or aluminum trichloride to give a γ-aryl -α,β-dihalo-$\Delta^{\alpha\beta}$- crotonolactone of Formula 15 (or the corresponding 3-acyl-3-haloacrylic acid or ester). When $R_1$, $R_2$ and $R_3$ are all hydrogen it is preferred that the para position of the phenol is blocked by a t-butyl group which may be removed at a later stage with aluminum chloride and an excess of a suitable aromatic compound such as toluene or anisole which can be easily alkylated under Friedel-Crafts condition. The compounds of Formula 16 may be converted into the compounds of Formula 13 by a series of reactions involving dehalogenation, e.g., by the use of hydrogen in the presence of a palladised charcoal catalyst, protection of the phenolic hydroxy, e.g., by using ethyl chloroformate, conversion of the pyridazinone into a 3-chloropyridazine, e.g., by using phosphoryl chloride, and deprotection of the protected phenolic hydroxyl, e.g., by treatment with mild alkali in the case of the ethoxycarbonyl derivative. The route outlined in Scheme 6 is

SCHEME 5
X represents Chlorine or Bromine
Y represents Chlorine or Methoxy

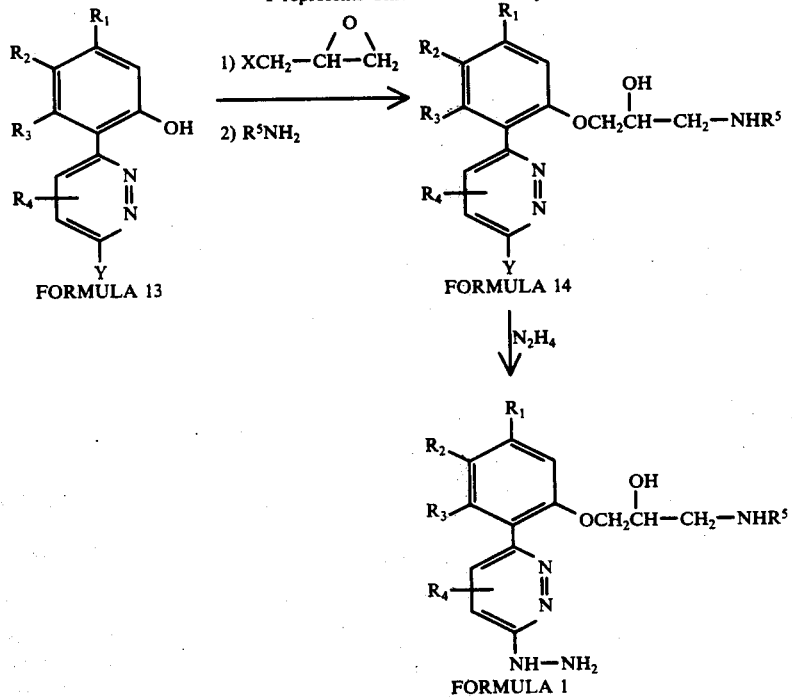

SCHEME 6

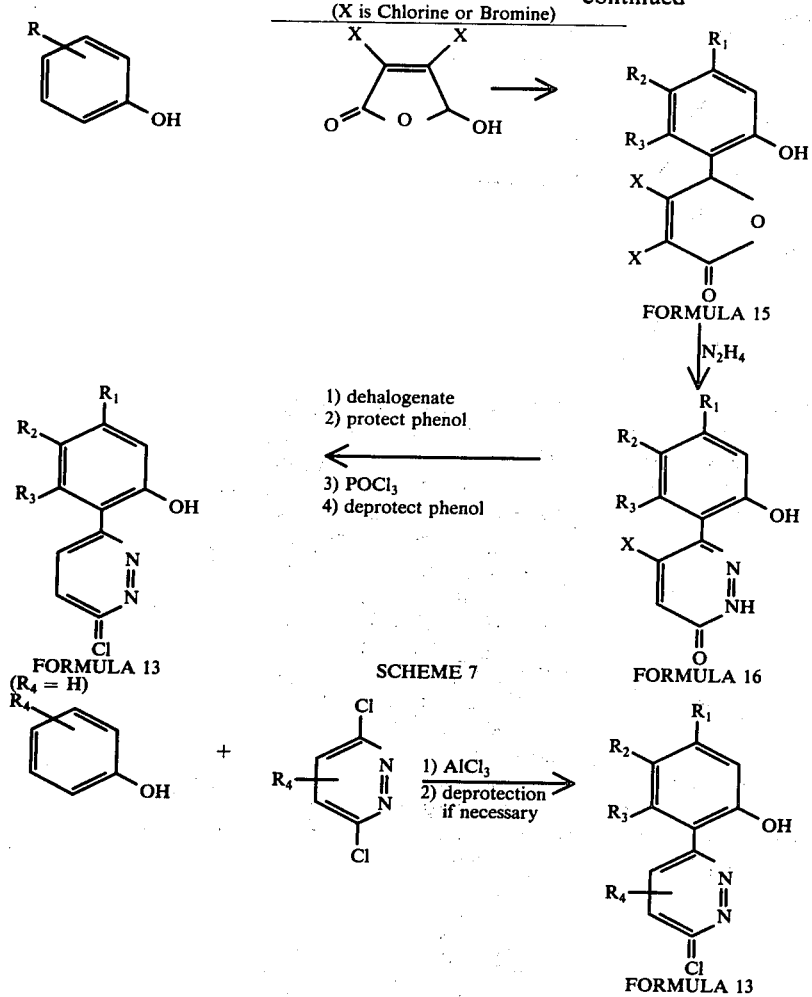

SCHEME 7 inappropriate when $R_1$, $R_2$ and $R_3$ are such that they are affected by conditions necessary for dehalogenation (e.g. when $R_1$, $R_2$ or $R_3$ is readily reducable).

An alternative procedure for the preparation of the phenylchloropyridazines of Formula 13 is outlined in Scheme 7.

A suitable phenol is treated with 3,6-dichloropyridazine and a suitable catalyst e.g., aluminium trichloride in a suitable solvent e.g., nitrobenzene to give a compound of Formula 13 by a Friedel-Crafts reaction. Preferably this reaction is used when the phenol is an activated phenol such as resorcinol. Preferably when the reaction is used to prepare a compound of Formula 13 wherein $R_1$, $R_2$ and $R_3$ are all hydrogen the phenol starting material has a paraprotecting group, such as t-butyl.

As stated above, the compounds of Formula I are β-adrenergic blocking agents and vasodilators. β-Adrenergic blocking agents are useful in the treatment of angina pectoris, cardiac arrhythmias and hypertension and vasodilators are often used in the treatment of hypertension. It will be appreciated that the compounds of the present invention which exhibit concomitant β-adrenergic blocking and vasodilator activity such as to cause a fall in blood pressure without tachycardia in man, are particularly useful. The β-adrenergic blocking activity of our compounds may be demonstrated in a suitable test preparation such as cats anaesthetised with pentobarbitone sodium (Nembutal), 60 mg/Kg i.p. In such anaesthetised cats, intravenous injections of isoprenaline cause tachycardia, and vasodilatation in the hind-limb. These effects of isoprenaline, which are dose-dependent and are due to stimulation of β-adrenoreceptors, can be reduced or abolished by intravenous administration of from 0.01 to 100 micromoles/Kg of the β-adrenergic blocking agent of Formula I.

Two tests may be used in the estimation of vasodilatation. In the first of these, the fall in blood pressure is measured in rats of a spontaneously hypertensive strain to which our compounds have been subcutaneously or orally administered in a concentration of from 0.1 to 1000 micromoles/Kg. Over a period of 6 hours commencing one hour before the administration of the compound the blood pressure and heart rate are monitored directly from indwelling polythene cannulae placed in the carotid artery. In the second test vasodilatation is measured directly as a decrease in vascular resistance of the autoperfused hindquarters of anaesthetised rats injected intra-arterially or intravenously with from 0.1 to 100 micromoles/Kg. of a compound of Formula I.

For therapeutic use, the pharmacologicaly active compounds of the present invention will normally by administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric, acetic, citric and maleic acids.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Examplary of liquid carriers are syrup, peanut oil, olive oil, water and the like.

A wide variety of pharmaceutical forms can be employed.

Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 500 mg. If a liquid carrier is used, the preparation may be in the form of a syrup, emulsion, soft gelatin capsule, sterile injectable liquid such as in an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to produce $\beta$-adrenergic blockade and vasodilatation. The route of administration may be oral or parenteral.

Preferably, each dosage unit will contain the active ingredient in an amount of from about 25 mg to about 500 mg most preferably from about 50 mg to about 250 mg.

The active ingredient will preferably be administered in equal doses one to three times per day. The daily dosage regimen will preferably be from about 100 mg to about 2 g.

Other pharmacologically active compounds may in certain cases be included in the composition. Advantageously the composition will be made up in a dosage unit form appropriate to the desired mode of administration for example as a tablet, capsule or injectable solution.

The invention is illustrated but in no way limited by the following examples, wherein all temperatures are given in degrees centigrade:

EXAMPLE 1

Preparation of 3-Hydrazino-6-[2-(2-hydroxy-3-isopropylaminopropoxy)phenyl]pyridazine i. Hydrogen chloride was bubbled into a gently boiling solution of the known 3-(2-hydroxybenzoyl)propionic acid (10 g. 0.05 mole) in dry methanol (20 ml) until esterification was complete. The solution was poured into ice-water and the ester extracted into dichloromethane. The organic solution was washed with water and evaporated to give methyl 3-(2-hydroxybenzoyl)propionate (10.55 g, 98%) as a pale yellow oil.

ii. A well stirred mixture of methyl 3-(2-hydroxybenzoyl)propionate (63.3 g, 0.3 mole), potassium carbonate (48.4 g, 0.35 mole), epibromohydrin (117 ml, 1.4 mole), and dry ethyl methyl ketone (2000 ml) was heated under reflux for 28 hours. Evaporation of the filtered solution under reduced pressure gave methyl 3-[2-(2,3-epoxypropoxy)benzoyl]-propionate (83 g, 100%). (Found: M+, 264; $C_{14}H_{16}O_5$ requires M, 264).

iii. A stirred mixture of methyl 3-[2-(2,3-epoxypropoxy)benzoyl]propionate (8.3 g, 0.031 mole), and isopropylamine (16.4 ml, 0.19 mole) was heated under reflux for 90 minutes. Evaporation of the solution under reduced pressure gave methyl 3-[2-(2-hydroxy-3-isopropylaminopropoxy)benzoyl]-propionate (10.2 g, 100%) as a pale brown oil.

iv. Hydrazine hydrate (4.65 ml, 0.09 mole) was added to a solution of methyl 3-[2-(2-hydroxy-3-isopropylaminopropoxy)-benzoyl]propionate (10 g, 0.03 mole) in glacial acetic acid (80 ml) and the solution was heated under reflux for one hour. Evaporation under reduced pressure gave an oil (25.5 g) which was dissolved in water, treated with an excess of sodium carbonate solution and extracted with dichloromethane. Evaporation of the dried extracts gave an oil (10.3 g) which was purified on a silica column by elution with a mixture of chloroform and methanol to give 6-[2-(2-hydroxy-3-isopropylaminopropoxy)phenyl]-4,5-dihydro-3(2H)-pyridazinone (6.25 g, 66%), m.p. 124°–126°. The hydrochloride, crystallised from 2-propanol, had m.p. 162°–5°–164.5°. (Found; C, 55.95; H, 7.19; Cl, 10.28; N, 12.09; M+, 305. $C_{16}H_{24}ClN_3O_3$ requires: C, 56.22; H, 7.08; Cl, 10.37; N, 12.29%; M(base),305).

v. A stirred mixture of 6-[2-(2-hydroxy-3-isopropylaminopropoxy)phenyl]-4,5-dihydro-3(2H)-pyridazinone (10 g, 0.03 mole), acetic anhydride (50 ml), acetic acid (50 ml) and pyridine (10 drops) was heated in a water bath held at 65°–75°. After 45 minutes, bromine (5.25 g, 0.03 mole) in acetic acid (40 ml) was added dropwise during 45 minutes. Evaporation under reduced pressure gave an oil which was dissolved in dichloromethane and washed with dilute hydrochloric acid and water. The dried organic solution was evaporated to an oil (15 g) which was purified on a silica column by elution with mixtures of chloroform and methanol. 6-[2-(2-Acetoxy-3-N-acetylisopropylaminopropoxy)phenyl]-3(2H)-pyridazinone was obtained as a glass (8.9 g, 70%) by evaporation under reduced pressure. (M+, 387; M, 387)

vi. Phosphorus pentasulphide (8.5 g, 0.04 mole) was added to a stirred solution for 6-[2-(2-acetoxy-3-N-acetylisopropylaminopropoxy)phenyl]-3(2H)-pyridazinone (7.4 g, 0.02 mole) in pyridine (160 ml) and the stirred mixture was heated under reflux for 1 hour. Additional phosphorus pentasulphide (4.25 g, 0.02 mole) was added and the stirred mixture was refluxed for a further hour. The cold supernatant pyridine solution was decanted (from a viscous oil), diluted with water and evaporated. The residue was dissolved in dichloromethane and washed with dilute hydrochloric acid and water. Evaporation of the dried organic solution gave an orange gum (7 g) which was separated on a silica column by elution with mixtures of chloroform and methanol into 6-[2-(2-acetoxy-3-N-thioacetylisopropylaminopropoxy)phenyl]-3(2H)-pyridazinethione (yellow glass, 4.2 g, 52%) and 6-[2-(2-acetoxy-3-N-acetylisopropylaminopropoxy)phenyl]-3(2H)-pyridazinethione (yellow glass, 2.0 g, 26%). (M+ (acetyl), 403; M 403. M+ (thioacetyl), 419; M 419)

vii. Aqueous sodium hydroxide solution (N/1, 57.2 ml) was added to a stirred solution of 6-[2-(2-acetoxy-3-N-thioacetylisopropylaminopropoxy)phenyl]-3(2H)-pyridazinethione (6 g, 0.014 mole) in methanol and the mixture was heated under reflux for 90 minutes. Sodium hydroxide (0.56 g, 0.014 mole) was added and the stirred mixture was refluxed for a further 2.5 hours. The residue after evaporation was dissolved in a small volume of water and the stirred solution was neutralised with 25% aqueous acetic acid to give a pale yellow precipitate, which was collected and washed with water (4.23 g, 92%, m.p. 162°–164° C).

Recrystallisation from water gave 6-[2-(2-hydroxy-3-isopropylaminopropoxy)phenyl]-3(2H)-pyridazinethione (m.p. 165.5°–167.5°), similarly prepared from 6-[2-(2-acetoxy-3-N-acetylisopropylaminopropoxy)phenyl]-3(2H)-pyridazinethione.

(Found: C, 60.15; H, 6.83; N, 13.2; M+, 319. $C_{16}H_{21}N_3O_2$ requires: C, 60.20; H, 6.63; N, 13.15%; M, 319).

viii. A stirred mixture of 6-[2-(2-hydroxy-3-isopropylaminopropoxy)phenyl]-3(2H)-pyridazinethione (1.5 g, 0.005 mole) and hydrazine hydrate (30 ml) was heated under reflux in an atmosphere of nitrogen for 90 minutes. Excess of hydrazine hydrate was removed under reduced pressure to give 3-hydrazino-6-[2-(2-hydroxy-3-isopropylaminopropoxy)phenyl]-pyridazine as an oil which was converted into an amorphous citrate (2 g, 83%).

(Found: C, 51.34; H, 5.93; N, 13.00; $C_{16}H_{23}N_5O_2 \cdot C_6H_8O_7 \cdot \frac{1}{2}CH_3OH$ requires: C, 51.40; H, 6.33; N, 13.32%).

EXAMPLE 2

Preparation of 3-[2-(3-t-Butylamino-2-hydroxypropoxy)phenyl]-6-hydrazinopyridazine i. A stirred mixture of methyl 3-[2-(2,3-epoxypropoxy)benzoyl]propionate (54.75 g, 0.21 mole), methanol (580 ml) and t-butylamine (140 ml, 1.31 mole) was heated under reflux for 70 minutes. Evaporation of the solution under reduced pressure gave an oil (73 g) which crystallised when allowed to stand. Purification on a silica column by elution with mixtures of chloroform and methanol gave methyl 3-[2-(3-t-butylamino-2-hydroxypropoxy)benzoyl]propionate (55.4 g, 80%) which after recrystallisation from benzene-petroleum ether (b.p. 60°–80°) had m.p. 80°–81.5°.

(Found: C, 63.63; H, 7.99; N, 3.90; M+, 337. $C_{18}H_{27}NO_5$ requires: C, 64.09; H, 8.07; N, 4.15%, M, 337)

ii. Hydrazine hydrate (22 ml, 0.44 mole) was added to a stirred solution of methyl 3-[2-(3-t-butylamino-2-hydroxypropoxy)benzoyl]propionate (48.8 g; 0.14 mole) in glacial acetic acid (500 ml) and the solution was heated under reflux for 90 minutes. Evaporation under reduced pressure gave an oil (127 g) which was dissolved in water, treated with an excess of sodium carbonate solution and extracted with dichloromethane. Evaporation of the dried extracts gave an oil (49 g) which was purified on a silica column by elution with mixtures of chloroform and methanol to give 6-[2-(3-t-butylamino-2-hydroxypropoxy)phenyl]-4,5-dihydro-3(2H)-pyridazinone (33.44 g, 72%, m.p. 138°–141°). The hydrochloride, crystallised from ethanol-ether, had m.p. 201°–203°.

(Found: C, 57.18; H, 7.41; Cl, 9.67; N, 11.39; M+, 319. $C_{17}H_{25}N_3O_3 \cdot HCl$ requires: C, 57.36; H, 7.36; Cl, 9.96; N, 11.81; M(base), 319). iii. A stirred mixture of 6-[2-(3-t-butylamino-2-hydroxypropoxy)phenyl]-4,5-dihydro-3(2H)-pyridazinone (15 g, 0.047 mole), acetic anhydride (100 ml) potassium carbonate (6.5 g, 0.047 mole) and pyridine (15 drops) was heated in a water bath whose temperature was rasied from 50° to 100° during 60 minutes. Acetic acid (100 ml) was added and the stirred mixture was heated in a water bath held at 75°. Bromine (7.52 g, 0.047 mole) in acetic acid (30 ml) was added dropwise during 60 minutes, and the mixture was heated for an additional 20 minutes. The residue after evaporation was dissolved in dichloromethane and washed with water. Evaporation of the dried organic solution gave a glass (17.4 g, 92%) which was purified on a silica column by elution with mixtures of chloroform and methanol to give 6-[2-(2-acetoxy-3-N-acetyl-t-butylaminopropoxy)phenyl]-3(2H)-pyridazinone (13.3 g, 70%) obtained as a glassy foam by evaporation under reduced pressure.

(Found: M+, 401; $C_{21}H_{27}N_3O_5$. requires: M, 401).

iv. Phosphorus pentasulphide (9g, 0.04 mole) was added to a stirred solution of 6-[2-(2-acetoxy-3-N-acetyl-t-butylaminopropoxy)phenyl]-3(2H)-pyridazinone (8.14 g, 0.02 mole) in dry pyridine (160 ml) and the stirred mixture was heated under reflux for 1.75 hours. Additional phosphorus pentasulphide (3 g, 0.013 mole) was added to the partly cooled mixture which was then refluxed for a further 1.75 hours. When cool the supernatant pyridine solution was decanted (from a viscous oil) and diluted with an equal volume of water. After evaporation, the residue was dissolved in dichloromethane and washed with dilute hydrochloric acid and with water. Evaporation of the dried organic solution gave a yellow foam (8.16 g, 96%). Purification on a silica column by elution with mixtures of chloroform and methanol gave 6-[2-(2-acetoxy-3-N-acetyl-t-butylaminopropoxy)phenyl]-3(2H)-pyridazinethione (7.44 g, 88%) as a yellow foam after evaporation under reduced pressure.

(Found: M+, 417. $C_{21}H_{27}N_3O_4S$ requires M, 417).

v. Aqueous sodium hydroxide solution (N/1, 71.4 ml) was added to a stirred solution of 6-[2-(2-acetoxy-3-N-acetyl-t-butylaminopropoxy)phenyl]-3(2H)-pyridazinethione (7.44g, 0.018 mole) in methanol (110 ml) and the mixture was heated under reflux for 30 minutes. The residue after evaporation was dissolved in water and the solution treated with 25% aqueous acetic acid to give pale yellow precipitate, which was collected and washed with water (5.64 g, 95% m.p. 184°–186.5°). Recrystallisation from aqueous ethanol gave 6-[2-(3-t-butylamino-2-hydroxypropoxy)phenyl]-3(2H)-pyridazinethione, m.p. 186.5°–189°.

(Found: C, 61.50; H, 6.78; N, 12.44; M+, 333. $C_{17}H_{23}N_3O_2S$ requires: C, 61.23; H, 6.95; N, 12.60% M, 333).

vi. A stirred mixture of 6-[2-(3-t-butylamino-2-hydroxypropoxy)phenyl]-3(2H)-pyridazinethione (2 g, 0.006 mole) and hydrazine hydrate (50 ml) was heated under reflux in an atmosphere of nitrogen for 90 minutes. Excess of hydrazine hydrate was removed under reduced pressure and 3-[2-(3-t-butylamino-2-hydroxypropoxy)phenyl]-6-hydrazinopyridazine was isolated as an oil which was characterised as the hemisulphate hemihydrate (2.34 g, 98%, m.p. 180°–185°). Recrystallisation from aqueous ethanol gave a crystalline material of m.p. 200°–203° (decomposition).

(Found: C, 52.41; H, 6.76; N, 17.78; M+, 331. $C_{17}H_{25}N_5O_2 \cdot \frac{1}{2}H_2SO_4 \cdot \frac{1}{2}H_2O$ requires: C, 52.43; H, 6.99; N, 17.98% M(base), 331).

EXAMPLE 3

Preparation of
3-[2-(3-t-Butylamino-2-hydroxypropoxy)-4-methylphenyl]-6-hydrazinopyridazine.

i. 3-(2-Hydroxy-4-methylbenzoyl)propionic acid was esterified with methanol-hydrogen chloride, in a similar manner to the procedure described in Example 1 (i), to give methyl 3-(2-hydroxy-4-methylbenzoyl)propionate, m.p. 61°–63°.

ii. Methyl 3-(2-hydroxy-4-methylbenzoyl)propionate was reacted wtih epibromohydrin in a similar manner to the procedure described in Example 1 (ii) to give methyl 3-[2-(2,3-epoxypropoxy)-4-methylbenzoyl]propionate, m.p. 61.5°–63°.

iii. Methyl 3-[2-(2,3-epoxypropoxy)-4-methylbenzoyl]-propionate was treated with t-butylamine in a similar manner to the procedure described in Example 2(i) to give methyl 3-[2-(3-t-butylamino-2-hydroxypropoxy)-4-methylbenzoyl]-propionate, m.p. 82°–84.5°.

iv. By subjecting methyl 3-[2-(3-t-butylamino-2-hydroxypropoxy)-4-methylbenzoyl]propionate to a series of reactions similar to that described in Example 2(ii–vi), the title compound may be produced.

EXAMPLE 4

3-[2-(3-t-Butylamino-2-hydroxypropoxy)-4-chlorophenyl]-6-hydrazinopyridazine i. Hydrogen chloride was bubbled into a gently boiling solution of 3-(4-chloro-2-hydroxybenzoyl)propionic acid (12.0 g, 0.053 mole) in dry ethanol (21.2 cc) until esterification was complete. The product crystallised from ether to give ethyl 3-(4-chloro-2-hydroxybenzoyl)propionate (13.29g, 98%, m.p. 68°–69°).

(Found: C, 56.07; H, 5.06; Cl, 13.69; M+, 256/258. $C_{12}H_{13}ClO_4$ requires; C, 56.15; H, 5.10; Cl, 13.81%; M, 256/258).

ii. A well stirred mixture of ethyl 3-(4-chloro-2-hydroxybenzoyl)propionate (9.6 g, 0.037 mole), potassium carbonate (5.96 g, 0.043 mole) epibromohydrin (14.4 ml, 0.173 mole) and dry butan-2-one (250 ml) was heated under reflux for 28 hours. Evaporation of the filtered solution under reduced pressure and purification of the residue by column chromatography gave ethyl 3-[4-chloro-2-(2,3-epoxypropoxy)benzoyl]-propionate as an oil (10.0 g, 86%).

(Found: M+, 312/314. $C_{15}H_{17}ClO_5$. requires M, 312/314).

iii. A stirred mixture of ethyl 3-[4-chloro-2-(2,3-epoxypropoxy)benzoyl]propionate (3.0 g, 0.01 mole) methanol (28 ml) and t-butylamine (6.7 ml, 0.0625 mole) was heated under reflux for 70 minutes. The mixture was evaporated to an oily residue which was purified on a silica column by elution with mixtures of chloroform and methanol and recrystallisation from ether-petroleum ether (b.p. 40°–60°) to give ethyl 3-[2-(3-t-butylamino-2-hydroxypropoxy)-4-chlorobenzoyl]propionate (3.18 g, 88%, m.p. 70°).

(Found: C, 58.93; H, 7.16; Cl, 9.64; N, 3.63; M+, 385/387. $C_{19}H_{28}ClNO_5$ requires; C, 59.14; H, 7.13; Cl, 9.19; N, 3.63%; M, 385/387).

iv. Hydrazine hydrate (1.57 ml, 0.0314 mole) was added to a stirred solution of ethyl 3-[2-(3-t-butylamino-2-hydroxypropoxy)-4-chlorobenzoyl]propionate (2.4 g, 0.0065 mole) in glacial acetic acid (36 ml) and the solution was heated under reflux for 90 minutes. Evaporation under reduced pressure gave an oil which was dissolved in water, treated with an excess of aqueous sodium carbonate solution and the mixture was extracted with dichloromethane. Evaporation of the dried organic extracts gave an oil which ws purified on a silica column by elution with mixtures of chloroform and methanol to give 6-[2-(3-t-butylamino-2-hydroxypropoxy)-4-chlorophenyl]-4,5-dihydro-3(2H)-pyridazinone (1.1 g, 50%, m.p. 195°). The hemisulphate, crystallised from ethanol, had m.p. 250° (decomposition).

(Found: C, 50.19; H, 6.21; Cl, 8.75; N, 10.11; S, 3.89; M+, 353/355. $C_{17}H_{24}ClN_3O_3.0.53\ H_2SO_4$ requires; C, 50.31; H, 5.96; Cl, 8.74; N, 10.35; S, 4.17%; S, 4.17%; M(base), 353/355).

v. By subjecting 6-[2-(3-t-butylamino-2-hydroxypropoxy)-4-chlorophenyl]-4,5-dihydro-3(2H)-pyridazinone to a similar series of reactions to that described in Example 2(iii–vi) the title compound may be prepared.

In a similar manner 3-[2-(3-t-Butylamino-2-hydroxypropoxy-4-bromophenyl]-6-hydrazinopyridazine may be prepared from 3-(4-bromo-2-hydroxybenzoyl)propionic acid

EXAMPLE 5

Preparation of
3-[2-(3-t-Butylamino-2-hydroxypropoxy)-6-fluorophenyl]-6-hydrazinopyridazine i. A cold solution of 2-fluoro-6-methoxylithiobenzene in ether was added to a cold dilute benzene solution of β-carbomethoxypropionyl chloride and the resulting complex was decomposed with ammonium chloride solution to give methyl 3-(2-fluoro-6-methoxybenzoyl)propionate.

ii. Methyl 3-(2-fluoro-6-methoxybenzoyl)propionate was demethylated with aluminium chloride in chlorobenzene and 3-(2-fluoro-6-hydroxybenzoyl)propionic acid was isolated.

iii. By subjecting 3-(2-fluoro-6-hydroxybenzoyl)propionic acid to a series of reactions similar to those described in Example 1(i–ii) and 2(i–vi), the title compound may be prepared.

EXAMPLE 6

Preparation of
6-[2-(3-t-Butylamino-2-hydroxypropoxy)-4-trifluoromethylphenyl]-3-hydrazinopyridazine i. A solution of 2-methoxy-5-trifluoromethylphenyllithium in ether was added to a cold stirred solution of N-methylsuccinimide in benzene. The resultant mixture was allowed to stand overnight and was then decomposed with ammonium chloride solution to give N-methyl 3-(2-methoxy-5-trifluoromethylbenzoyl)propionamide.

ii. N-Methyl 3-(2-methoxy-5-trifluoromethylbenzoyl)-propionamide was demethylated with hydrogen bromide in acetic acid and 3-(2- hydroxy-5-trifluoromethylbenzoyl)-propionic acid was isolated.

iii. By subjecting 3-(2-hydroxy-5-trifluoromethylbenzoyl)-propionic acid to a series of reactions similar to those described in Examples 1(i–ii) and 2(i–vi), the title compound may be prepared.

EXAMPLE 7

6-[2-(3-t-Butylamino-2-hydroxypropoxy)-4-methoxyphenyl]-3-hydrazinopyridazine a. i. 3-Chloro-6-(2,4-dihydroxyphenyl)pyridazine (4.0 g, 0.18 mole), dimethyl sulphate (2.55 g, 0.0201 mole), potassium carbonate (10.0 g, 0.072 mole) and dry acetone (100 ml) were stirred at room temperature for 20 hours. The reaction mixture was filtered and the inorganic residue was washed with more acetone. Evaporation of the combined filtrates gave a brown residue which was extracted wth dilute sodium hydroxide solution. The aqueous extract was washed with dichloromethane, treated with charcoal, filtered and acidified. The resulting precipitate was collected, washed with water and crystallised from ethanol to give 3-chloro-6-(2-hydroxy-4-methoxyphenyl)-pyridazine (2.2 g, 49%; m.p. 156°–157°).

ii. A stirred solution of 3-chloro-6-(2-hydroxy-4-methoxyphenyl)pyridazine (2.0 g, 0.0085 mole), and sodium methoxide (5.0 g, 0.093 mole), in dry methanol (50 ml) was heated under reflux for 24 hours. Glacial acetic acid (5.5 ml, 0.096 mole) was then added to the red reaction mixture and the resulting suspension was evaporated to dryness. Water was added to the residue and the crude product was collected, washed with water and dried. 6-(2-Hydroxy-4-methoxyphenyl)-3-methoxypyridazine crystallised from methanol (1.6 g, 80%; m.p. 136°–137°).

iii. A well-stirred mixture of 6-(2-hydroxy-4-methoxyphenyl)-3-methoxypyridazine (1.3 g, 0.0056 mole), epibromohydrin (3.8 g, 0.028 mole), potassium carbonate (5.0 g, 0.036 mole) and dry butan-2-one (60 ml) was heated under reflux for 24 hours. The filtered solution was then evaporated leaving a red oil which was purified on a silica column by elution with dichloromethane-methanol mixtures. 6-[2-(2,3-Epoxypropoxy)-4-methoxyphenyl]-3-methoxypyridazine crystallised from ether (0.8g, 50%; m.p. 83°–84°).

iv. A solution of 6-[2-(2,3-epoxypropoxy)-4-methoxyphenyl]-3-methoxypyridazine (0.7 g, 0.0024 mole), t-butylamine (10.0 ml, 0.093 mole) in methanol (20 ml) was allowed to stand at room temperature for 24 hours. Evaporation of the solvent and crystallisation of the residue from ethyl acetate gave 6-[2-(3-t-butylamino-2-hydroxypropoxy)-4-methoxyphenyl]-3-methoxypyridazine (0.62 g, 70%, m.p. 114°–116°).

v. A stirred mixture of 6-[2-(3-t-butylamino-2-hydroxypropoxy)-4-methoxyphenyl]-3-methoxypyridazine (0.36 g, 0.001 mole) and hydrazine hydrate (8 ml) was heated under reflux for 2 hours. Excess of hydrazine hydrate was removed under reduced pressure and 6-[2-(3-t-butylamino-2-hydroxypropoxy)-4-methoxyphenyl]-3-hydrazino pyridazine was isolated by crystallisation from ethanol-ether.

b. i. A stirred mixture of 6-chloro-3-(2-hydroxy-4-methoxyphenyl)pyridazine (0.1 mole), potassium carbonate (0.3 mole) and epibromohydrin (0.4 mole) in butan-2-one was heated under reflux overnight. The filtered solution was evaporated to give an oil which was purified by elution with mixtures of chloroform-methanol on a silica column to give 6-chloro-3-[2-(2,3-epoxypropoxy)phenyl]pyridazine.

ii. A solution of 6-chloro-3-[2-(2,3-epoxypropoxy)-4-methoxyphenyl]pyridazine (0.05 mole) and t-butylamine (0.5 mole) in methanol was allowed to stand at room temperature for 40 hours. Evaporation of the reaction mixture gave 6-chloro-3-[2-(3-t-butylamino-2-hydroxypropoxy-4-methoxyphenyl]-pyridazine.

iii. A stirred mixture of 6-chloro-3-[2-(3-t-butylamino-2-hydroxypropoxy)-4-methoxyphenyl]pyridazine and hydrazine hydrate in ethanol was heated under reflux for 3 hours. Evaporation of the reaction mixture under reduced pressure gave the title compound.

c. i. A mixture of 3-[2-(3-t-butylamino-2-hydroxypropoxy)-4-methoxyphenyl]-6-chloro-pyridazine, t-butyl carbazate and 1,8-bis-(dimethylamino)naphthalene was heated for 2 hours to give 3-[2-(3-t-butylamino-2-hydroxypropoxy)-4-methoxyphenyl]-6-(2-t-butyloxycarbonylhydrazino)pyridazine.

ii. 3-[2-(3-t-Butylamino-2-hydroxypropoxy)-4-methoxyphenyl]-6-methoxypyridazine was heated with t-butyl carbazate to give 3-[2-(3-t-butylamino-2-hydroxypropoxy)-4-methoxyphenyl]-6-(2-t-butyloxycarbonylhydrazino)pyridazine.

iii. 3-[2-(3-t-Butylamino-2-hydroxypropoxy)-4-methoxyphenyl]-6-(2-t-butyloxycarbonylhydrazino)pyridazine (0.01 mole) was treated with dilute sulphuric acid (0.01 mole) and the solution evaporated to dryness to give the title compound as its sulphate salt.

d. i. A mixture of 6-chloro-3-(2-hydroxy-4-methoxyphenyl)-pyridazine, t-butyl carbazate and 1,8-bis-(dimethylamino)-naphthalene was heated for 2 hours to give 6-(2-t-butyloxycarbonylhydrazino)-3-(2-hydroxy-4-methoxyphenyl)pyridazine.

ii. A stirred mixture of 6-(2-t-butyloxycarbonylhydrazino)-3-(2-hydroxy-4-methoxyphenyl)pyridazine, epibromohydrin and potassium carbonate in butan-2-one was heated under reflux overnight. Evaporation of the filtered solution gave an oil which was purified by elution with mixtures of dichloromethane-methanol on silica to give 6-(2-t-butyloxycarbonylhydrazino)-3-[2,3-epoxypropoxy)-4-methoxyphenyl]pyridazine.

iii. A solution of 6-(2-t-butyloxycarbonylhydrazino)-3-[2-(2,3-epoxypropoxy)-4-methoxyphenyl]pyridazine and t-butylamine in methanol was allowed to stand at room temperature for 48 hours. Evaporation of the reaction mixture gave 3-[2-(3-t-butylamino-2-hydroxypropoxy)-4-methoxyphenyl]-6-(2-t-butyloxycarbonylhydrazino)pyridazine.

EXAMPLE 8

3-[4-Allyloxy-2-(3-t-butylamino-2-hydroxypropoxy)-phenyl]-6-hydrazinopyridazine i. 3-Chloro-6-(2,4-dihydroxyphenyl)pyridazine was reacted with allyl bromide under similar conditions to those described in Example 7a(i), to give 6-(4-allyloxy-2-hydroxyphenyl)-3-chloropyridazine.

ii. 6-(4-Allyloxy-2-hydroxyphenyl)-3-chloropyridazine was employed in a series of reactions similar to those described in Example 7b(i–iii) to give the title compound.

EXAMPLE 9

Preparation of
3-[2-(3-t-Butylamino-2-hydroxypropoxy)-4-hydroxyphenyl]-6-hydrazinopyridazine i. 3-Chloro-6-(2,4-dihydroxyphenyl)pyridazine (1 mole) was treated with ethyl chloroformate (1.1 mole) in pyridine to give 3-chloro-6-(4-ethoxycarbonyloxy-2-hydroxyphenyl)pyridazine.

ii. 3-Chloro-6-(4-ethoxycarbonyloxy-2-hydroxyphenyl)pyridazine was employed in a series of reactions similar to those described in Example 7b (i–ii) and the product dissolved in dilute sodium hydroxide solution and the solution treated with acid to give 3-[2-(3-t-butylamino-2-hydroxypropoxy)-4-hydroxyphenyl]-6-chloropyridazine.

iii. 3-[2-(3-t-Butylamino-2-hydroxypropoxy)-4-hydroxyphenyl]-6-chloropyridazine was reacted with hydrazine hydrate under similar conditions to those described in Example 7b(iii) to give the title compound.

EXAMPLE 10

Preparation of
3-[2-(3-t-Butylamino-2-hydroxypropoxy)-6-methoxyphenyl]-6-hydrazinopyridazine.

i. A solution of 1,3-dimethoxybenzene (89 ml, 0.064 mole) in dry tetrahydrofuran (480 ml) was added during 10 minutes to a stirred solution of n-butyl lithium in hexane (350 ml, 0.6 mole) under an atmosphere of nitrogen. The stirred mixture was heated under reflux for 90 minutes, then a solution of N-methyl succinimide (77 g, 0.68 mole) in dry tetrahydrofuran was added dropwise. The mixture was heated under reflux for an additional hour and then allowed to stand overnight. The supernatant was decanted and the residue was hydrolysed with 20% aqueous ammonium chloride solution (280 ml) and extracted with chloroform. The washed and dried extract was evaporated and the residue recrystallised from ethyl acetate to give N-methyl 3-(2,6-dimethoxybenzoyl)propionamide (15 g, 10%, m.p. 134°).

(Found: C. 62.18; H, 6.73; N, 5.54; $C_{13}H_{17}NO_4$ requires C, 62.14; H, 6.82; N, 5.57%).

ii. N-Methyl 3-(2,6-dimethoxybenzoyl)propionamide was demethylated with ammonium chloride in chlorobenzene to give N-methyl 3-(2-hydroxy-6-methoxybenzoyl)propionamide, m.p. 125° which may also be prepared from a by-product, N-methyl 3-(2,6-dihydroxybenzoyl)propionamide, by selective methylation with methyl iodide and potassium carbonate in acetone.

iii. By subjecting N-methyl 3-(2-hydroxy-6-methoxybenzoyl)propionamide to a series of reactions similar to those described in Examples 1(i–ii) and 2(i–vi), the title compound may be prepared.

EXAMPLE 11

Preparation of
3-[2-(3-t-Butylamino-2-hydroxypropoxy)-5-cyanophenyl]-6-hydrozinopyridazine i. Aluminum chloride (148 g, 1.11 mole) was added to a stirred mixture of 4-cyanophenol (44 g, 0.37 mole), succinic anhydride (33.3 g, 0.33 mole), and sym-tetrachloroethane (260 ml), and the mixture was then heated at 135° for 2 hours. The resultant complex was decomposed with ice and hydrochloric acid, and 3-(5-cyano-2-hydroxybenzoyl)propionic acid was isolated by standard procedures.

ii. 3-(5-Cyano-2-hydroxybenzoyl)propionic acid was subjected to a series of reactions similar to those described in Example 1(i–ii) and 2(i–ii), to give 6-[2-(3-t-butylamino-2-hydroxypropoxy)-5-cyanophenyl]-4,5-dihydro-3(2H)-pyridazinone.

iii. A mixture of 6-[2-(3-t-butylamino-2-hydroxypropoxy)-5cyanophenyl]-4,5-dihydro-3(2H)-pyridazinone and chloramil was heated under reflux in n-butanol to give 6-[2-(3-t-butylamino-2-hydroxypropoxy)-5-cyanophenyl]-3(2H)-pyridazinone.

iv. 6-[2-(3-t-Butylamino-2-hydroxypropoxy)-5-cyanophenyl]-3(2H)-pyridazinone was acetylated with a mixture of acetic anhydride and potassium carbonate to give 6-[2-(2-acetoxy-3-N-acetyl-t-butylaminopropoxy)-5-cyanophenyl]-3(2H)-pyridazinone.

v. By subjecting 6-[2-(2-acetoxy-3-N-acetyl-t-butylaminopropoxy)-5-cyanophenyl]-3(2H)-pyridazinone to a series of reactions similar to those described in Example 2 (iv-vi), the title compound may be prepared.

EXAMPLE 12

Preparation of
3-[5-Carboxamidomethyl-2-(2-hydroxy-3-isopropylaminopropoxy)phenyl]-6-hydrazinopyridazine.

i. 4-Hydroxybenzyl cyanide was reacted with succinic anhydride and aluminum chloride in a similar manner to that described in Example 11(i) to give 3-(5-cyanomethyl-2-hydroxybenzoyl)propionic acid.

ii. 3-(5-Cyanomethyl-2-hydroxybenzoyl)propionic acid was subjected to a series of reactions similar to those described in Example 1(i–vi) to give 6-[5-cyanomethyl-2-(2-hydroxy-3-isopropylaminopropoxy)phenyl]-3(2H)-pyridazinethione.

iii. 6-[5-Cyanomethyl-2(2-hydroxy-3-isopropylaminopropoxy)phenyl]-3(2H)-pyridazinethione was dissolved in cold concentrated sulphuric acid and the solution poured into ice-water and neutralised to give 6-[5-carboxamidomethyl-2-(2-hydroxy-3-isopropylaminopropoxy)phenyl]-3(2H)-pyridazinethione.

iv. A mixture of 6-[5-carboxamidomethyl-2-(2-hydroxy-3-isopropylaminopropoxy)phenyl]-3(2H)-pyridazinethione, hydrazine hydrate, and ethanol was heated under reflux and then evaporated under reduced pressure to give the title compound.

EXAMPLE 13

3-[5-Amino-2-(3-t-butylamino-3-hydroxypropoxy)-phenyl]-6-hydrazinopyridazine i. Nitric acid (d. 1.52; 50 ml) was added dropwise to a stirred suspension of 3-(2-hydroxybenzoyl)propionic acid (30 g, 0.155 mole) in glacial acetic acid (250 ml) at 5°–10°. The temperature was allowed to rise slowly, at 30°–35° an exothermic reaction took place and cooling was necessary to keep the temperature of the reaction mixture below 45°, the resulting solution was stirred for a further 60 minutes and then poured into ice-water (750 ml). The yellow precipitate, a crude mixture of 3-(2-hydroxy-5-nitrobenzoyl)propionic acid and 3-(2-hydroxy-3-nitrobenzoyl)propionic acid, was washed with water and dried (36.0 g, 97%, m.p. 152°–156°).

(Found: M+, 239. $C_{10}H_9NO_6$ requires: M, 239).

ii. The above mixture of acids (60 g, 0.25 mole) was dissolved in dry methanol (800 ml) and hydrogen chloride gas was passed through the gently boiling solution for 2 hours. The solvent was evaporated under reduced pressure, the residue in chloroform (200 ml) was washed with aqueous sodium bicarbonate (200 ml) and with water. The dried solution was evaporated under reduced pressure to give a solid (55 g) which was separated into the isomeric esters on a silica column by elution with chloroformmethanol mixtures. The methyl 3-(2-hydroxy-5-nitrobenzoyl)propionate (25.3 g, 40%) was crystallised from carbon tetrachloride as needles (m.p. 90°–93°).

(Found: C, 52.16; H, 4.36; N, 5.38; M+, 253. $C_{11}H_{11}NO_6$ requires: C, 52.17; H, 4.38; N, 5.53%; M, 253).

iii. Methyl 3-(2-hydroxy-5-nitrobenzoyl)propionate (19.0 g, 0.075 mole) was dissolved in sodium hydroxide solution (2N; 600 ml) and heated on a steam bath for 1 hour. Acidification of the cooled solution with dilute hydrochloric acid gave 3-(2-hydroxy-5-nitrobenzoyl)-propionic acid which was washed with water and dried (17.4 g, 97%, m.p. 175°–178°).

iv. A solution of 3-(2-hydroxy-5-nitrobenzoyl)propionic acid (5.5 g, 0.023 mole) in ammonium hydroxide solution (5N; 100 ml) was added to a stirred, boiling solution of ferrous sulphate heptahydrate (45 g, 0.161 mole) in water (200 ml). Stirring under reflux was continued for a futher 1 hour, ammonium hydroxide solution was added to pH 9, the mixture was filtered through Kieselguhr and evaporated to dryness. The solid residue was crystallised from ethanol to give pale yellow needles of 3-(5-amino-2-hydroxybenzoyl)propionic acid (2.2 g, 46%, m.p. 158°-160°).

(Found: M+, 209. $C_{10}H_{11}NO_4$ requires: M, 209).

v. Sodium hydroxide solution (0.2 N) was added to 3-(5-amino-2-hydroxybenzoyl)propionic acid (2.4 g, 0.0115 mole) until the solid dissolved. Acetic anhydride (3.0 ml) was quickly added to the solution (pH 10) with vigorous stirring at 10°-15°, after which the pH was in the range 4-5, and stirring was continued for a further hour. The precipitated solid was collected and washed with water, and a second crop was obtained by evaporation of the filtrate and addition of water to the residue. The combined solids were recrystallised from ethanol to give 3-(5-acetamido-2-hydroxybenzoyl)propionic acid (2.2 g, 76%, m.p. 205°-206°).

(Found: C, 57.13; H, 5.25; N, 5.57; M+, 251. $C_{12}H_{13}NO_5$ requires: C, 57.37; H, 5.22; N, 5.58%; M, 251).

vi. Hydrogen chloride gas was passed through a gently boiling solution of 3-(5-acetamido-2-hydroxybenzoyl)propionic acid (1.2 g, 0.0048 mole) in dry methanol (20 ml) until esterification was complete. The reaction mixture was poured into ice-water and extracted with chloroform. The extract was washed with sodium bicarbonate solution and water, dried and evaporated to give methyl 3-(5-acetamido-2-hydroxybenzoyl)propionate (0.75 g, 59%, m.p. 145°-147°). (Found: M+, 265. $C_{13}H_{15}NO_5$ requires: M, 265).

vii. Methyl 3-(5-acetamido-2-hydroxybenzoyl)propionate (0.75 g, 0.0028 mole), anhydrous potassium carbonate (0.39 g, 0.0028 mole), epibromohydrin (0.78 g, 0.00565 mole) and dry ethyl methyl ketone (20 ml) were stirred and heated under reflux for 16 hours. The cooled mixture was filtered and evaporated under reduced pressure to an oil which was purified by elution from a silica column with chloroformmethanol to give methyl 3-[5-acetamido-2-(2,3-epoxypropoxy)benzoyl]propionate (0.52 g, 57%, m.p. 84°-87°).

(Found: M+, 321, $C_{16}H_{19}NO_6$ requires M, 321).

viii. A solution of methyl 3-[5-acetamido-2-(2,3-epoxypropoxy)benzoyl]propionate (0.52 g, 0.0016 mole), t-butylamine (20 ml) and methanol (10 ml) was heated under reflux for 16 hours. Evaporation of the reaction mixture left an oil which was dissolved in ethanol and treated with ether to give crystalline methyl 3-[5-acetamido-2-(3-t-butylamino-2-hydroxypropoxy)benzoyl]propionate (0.21 g, 33%; m.p. 127°-128°).

(Found; M+, 394. $C_{20}H_{30}N_2O_6$ requires: M, 394).

ix. Hydrazine hydrate (0.0785 ml, 0.00157 mole) was added to a stirred solution of methyl 3-[5-acetamido-2-(3-t-butylamino-2-hydroxypropoxy)benzoyl]propionate (0.21 g, 0.0005 mole) in glacial acetic acid (2 ml) and the solution was heated under reflux for 90 minutes. The residue after evaporation was treated with an excess of sodium bicarbonate solution and the solution evaporated to dryness under reduced pressure. The residue was extracted with dichloromethane and the dried extract evaporated to dryness. An aqueous solution of the residue was washed with two small portions of dichloromethane and then evaporated to an oily residue, which with ethyl acetate gave 6-[5-acetamido-2-(3-t-butylamino-2-hydroxypropoxy)phenyl]-4,5-dihydro-3(2H)-pyridazinone (0.16 g, 80%, m.p. 165°-168°).

x. 6-[5-Acetamido-2-(3-t-butylamino-2-hydroxypropoxy)phenyl]-4,5-dihydro-3(2H)-pyridazinone was reacted with chloranil in boiling butanol to give 6-[5-acetamido-2-(3-t-butylamino-2-hydroxypropoxy)phenyl]-3(2H)-pyridazinone.

xi. A solution of 6-[5-acetamido-2-(3-t-butylamino-2-hydroxypropoxy)phenyl]-3(2H)-pyridazinone in acetic anhydride containing potassium carbonate was heated on a steam bath for 1 hour to give 6-[5-acetamido-2-(2-acetoxy-3-N-acetyl-t-butylamino)phenyl]-3(2H)-pyridazinone.

xii. A stirred mixture of 6-[5-acetamido-2-(2-acetoxy-3-N-acetyl-t-butylamino)phenyl]-3(2H)-pyridazinone, phosphorus pentasulphide and pyridine was heated under reflux for 3 hours and the reaction mixture evaporated under reduced pressure. Purification of the product by elution with dichloromethane-methanol mixtures from a silica column gave fractions which contained 6-[5-acetamido-2-(2-acetoxy-3-N-acetyl-t-butylamino)-phenyl]-3(2H)-pyridazinethione and 6-[2-(2-acetoxy-3-N-acetyl-t-butylamino)-5-thioacetamidophenyl]-3(2H)-pyridazinethione.

xiii. Hydrolysis of the two column fractions from (xii) with sodium hydroxide in boiling methanol followed by neutralisation and evaporation of the reaction mixture gave 6-[5-amino-2-(3-t-butylamino-2-hydroxypropoxy)-phenyl]-3(2H)-pyridazinethione.

xiv. Reaction of 6-[5-amino-2-(3-t-butylamino-2-hydroxypropoxy)phenyl]-3(2H)-pyridazinethione with hydrazine hydrate under similar conditions to those described in Example 2(vi) gave the title compound.

EXAMPLE 14

3-[5-Acetamido-2-(3-t-butylamino-2-hydroxypropoxy)-phenyl]-6-hydrazinopyridazine.

i. Addition of acetic anhydride to a stirred suspension of 6-[5-amino-2-(3-t-butylamino-2-hydroxypropoxy)-phenyl]-3(3H)-pyridazinethione in an aqueous buffer solution at pH 5.5 gave 6-[5-acetamido-2-(3-t-butylamino-2-hydroxypropoxy)phenyl]-3(2H)-pyridazinethione.

ii. Reaction of 6-[5-acetamido-2-(3-t-butylamino-2-hydroxypropoxy)phenyl]-3(2H)-pyridazinethione with hydrazine hydrate in boiling ethanol followed by evaporation of the reaction mixture under reduced pressure gave the title compound.

EXAMPLE 15

6-Hydrazino-3-[2-(2-hydroxy-3-t-butylaminopropoxy-5-(methylamino)phenyl]pyridazine i. 3-[5-Amino-2-(3-t-butylamino-2-hydroxypropoxy)-benzoyl]-propionic acid, prepared by hydrolysis of the product of Example 13(viii), was esterified with hydrogen chloride in methanol. Evaporation of the solution under reduced pressure gave a residue which was dissolved in the minimum quantity of water, the solution was neutralised with sodium carbonate and extracted with dichloromethane. The extract was washed with saturated brine, dried and evaporated to give methyl 3-[5-amino-2-(2-hydroxy-3-t-butylaminopropoxy)benzoyl]-propionate.

ii. A solution of methyl 3-[5-amino-2-(2-hydroxy-3-t-butylaminopropoxy)benzoyl]propionate in dichloromethane was treated with excess of trifluoroacetic anhydride and potassium carbonate and the mixture was stirred until the reaction was complete. Water was added and the aqueous phase was extracted with dichloromethane. The extract was washed with water, dried and evaporated to give methyl 3-[5-trifluoroacetylamino-2-(2-trifluoroacetoxy-3-N-trifluoroacetyl-t-butylaminopropoxy)benzoyl]propionate.

iii. Methyl 3-[5-trifluoroacetylamino-2-(2-trifluoroacetoxy-3N-trifluoroacetyl-t-butylaminopropoxy)benzoyl]propionate was heated under reflux for 10 minutes with an excess of methyl iodide and powdered potassium hydroxide in dry acetone. Methyl iodide and the solvent were removed under reduced pressure and the residue, in water, was heated under reflux for 10 minutes. The solution was neutralised and evaporated under reduced pressure. The residue was extracted with hot ethanol, and the extracts were evaporated under reduced pressure to give 3-[2-(2-hydroxy-3-t-butylaminopropoxy)-5-(methylamino)benzoyl]propionic acid.

iv. 3-[2-(2-Hydroxy-3-t-butylaminopropoxy)-5-(methylamino)benzoyl]propionic acid was cyclised by a method similar to that described in Example 13(ix), to give 6-[2-(2-hydroxy-3-t-butylaminopropoxy)-5-(methylamino)phenyl]-4,5-dihydro-3(2H)-pyridazinone.

v. 6-[2-(2-Hydroxy-3-t-butylaminopropoxy)-5-(methylamino)phenyl]-4,5-dihydro-3(2H)-pyridazinone was treated with acetic anhydride in a manner similar to that described in Example 14(i) to give 6-[5-N-acetyl(-methylamino)-2-[2-hydroxy-3-t-butylaminopropoxy)-phenyl]-4,5-dihydro-3(2H)-pyridazinone.

vi. 6-[5-N-Acetyl(methylamino)-2-[2-hydroxy-3-t-butylaminopropoxy)phenyl]-4,5-dihydro-3(2H)-pyridazinone was employed in a sequence of reactions similar to those described in Example 13 (x–xiv) to give the title compound.

EXAMPLE 16

Preparation of 3-[2-(3-t-Butylamino-2-hydroxypropoxy)-5-nitrophenyl]-6-hydrazinopyridazine By subjecting methyl 3-(2-hydroxy-5-nitrobenzoyl)-propionate (prepared as in Example 13(ii)) to a series of reactions similar to those described in Example 1(ii) and 2(i–vi), the title compound may be prepared.

EXAMPLE 17

Preparation of 3-[2-(3-t-Butylamino-2-hydroxypropoxy)-5-dimethylaminophenyl]-6-hydrazinopyridazine i. A stirred mixture of 6-[2-(2-acetoxy-3-N-acetyl-t-butylaminopropoxy)-5-nitrophenyl]-3-(2H)-pyridazinone (from Example 16), ethanol, cyclohexene, and 10% palladium on charcoal, was heated under reflux for 16 hours to give 6-[5-amino-2-(2-acetoxy-3-N-acetyl-t-butylaminopropoxy)phenyl]-3-(2H)-pyridazinone.

ii. 6-[5-Amino-2-(2-acetoxy-3-N-acetyl-t-butylaminopropoxy)phenyl]-3(2H)-pyridazinone was treated with dimethyl sulphate and sodium acetate in aqueous ethanol to give 6-[2-(2-acetoxy-3-N-acetyl-t-butylaminopropoxy)-5-dimethylaminophenyl]-3(2H)-pyridazinone.

iii. By subjecting 6-[2-(2-acetoxy-3-N-acetyl-t-butylaminopropoxy)-5-dimethylaminophenyl]-3(2H)-pyridazinone to a series of reactions similar to those described in Example 2(iv-vi), the title compound may be prepared.

EXAMPLE 18

Preparation of 3-[2-(3-t-Butylamino-2-hydroxypropoxy)-5-carboxamidophenyl]-6-hydrazinopyridazine i. Aluminium chloride was added to a stirred mixture of 2-(4-hydroxyphenyl)acetamide, succinic anhydride, and symtetrachloroethane, and the mixture heated at 135° for 2 hours. The complex was decomposed with ice-hydrochloric acid and the solvent steam distilled to give 3-(3-carboxypropionyl)-4-hydroxybenzoic acid.

ii. 3-(3-Carboxypropionyl)-4-hydroxybenzoic acid was esterified with methanol-hydrogen chloride to give methyl 3-(3-carbomethoxypropionyl)-4-hydroxybenzoate.

iii. Methyl 3-(3-carbomethoxypropionyl)-4-hydroxybenzoate was subjected to a series of reactions similar to those described in Examples 1(ii) and 2(i) to give methyl 4-(3-t-butylamino-2-hydroxypropoxy)-3-(3-carbomethoxypropionyl) benzoate.

iv. Methyl 4-(3-t-butylamino-2-hydroxypropoxy)-3-(3-carbomethoxypropionyl)benzoate was heated with dilute sodium hydroxide solution until hydrolysis was complete. The solution was neutralised with acetic acid then evaporated under reduced pressure. Extraction of the residue with ethanol and evaporation of the extracts gave 4-(3-t-butylamino-2-hydroxypropoxy)-3-(3-carboxypropionyl)benzoic acid.

v. A solution of equimolar amounts of 4-(3-t-butylamino-2-hydroxypropoxy)-3-(3-carboxypropionyl)benzoic acid and hydrazine hydrate in water was heated under reflux for 16 hours. The volume of the solution was reduced in vacuo to give 4-(3-t-butylamino-2-hydroxypropoxy)-3-(1,4,5,6-tetrahydro-6-oxo-3-pyridazinyl)benzoic acid.

vi. A mixture of 4-(3-t-butylamino-2-hydroxypropoxy)-3-(1,4,5,6-tetrahydro-6-oxo-3-pyridazinyl)benzoic acid, chloranil, and n-butanol, was heated under reflux to give 4-(3-t-butylamino-2-hydroxypropoxy)-3-(1,6-dihydro-6-oxo-3-pyridazinyl)benzoic acid.

vii. 4-(3-t-Butylamino-2-hydroxypropoxy)-3-(1,6-dihydro-6-oxo-3-pyridazinyl)benzoic acid was esterified with ethanolhydrogen chloride to give ethyl 4-(3-t-butylamino-2-hydroxypropoxy)-3-(1,6-dihydro-6-oxo-3-pyridazinyl)benzoate.

viii. Ethyl 4-(3-t-butylamino-2-hydroxypropoxy)-3-(1,6-dihydro-6-oxo-3-pyridazinyl)benzoate was treated with acetic anhydride in the presence of potassium carbonate to give ethyl 4-(2-acetoxy-3-N-acetyl-t-butylaminopropoxy)-3-(1,6-dihydro-6-oxo-3-pyridazinyl)benzoate.

ix. Ethyl 4-(2-acetoxy-3-N-acetyl-t-butylaminopropoxy)-3-(1,6-dihydro-6-oxo-3pyridazinyl)benzoate was subjected to a series of reactions similar to those described in Example 2(iv-v) to give 4-(3-t-butylamino-2-hydroxypropoxy)-3-(1,6-dihydro-6-thiono-3-pyridazinyl)benzoic acid.

x. 4-(3-t-Butylamino-2-hydroxypropoxy)-3-(1,6-dihydro-6-thiono-3-pyridazinyl)benzoic acid was treated with hydrazine hydrate in boiling ethanol. The solution was evaporated under reduced pressure and the residue treated with t-butyl azidoformate in pyridine. After evaporation the residue was heated under reflux with acetone and the resultant mixture evaporated under reduced pressure to give 4-(3-t-butylamino-2-hydroxypropoxy)-3-[6-(2-t-butyloxycarbonylhydrazino)-3-pyridazinyl]benzoic acid.

xi. A solution of 4-(3-t-butylamino-2-hydroxypropoxy)-3-[6-(2-t-butyloxycarbonylhydrazine)-3-pyridazinyl]benzoic acid and ammonia in dioxan was treated with dicyclohexylcarbodiimide to give 3-[2-(3-t-butylamino-2-hydroxypropoxy)-5-carboxamido-phenyl]-6-(2-t-butyloxycarbonylhydrazino)pyridazine.

xii. 3-[2-(3-t-Butylamino-2-hydroxypropoxy)-5-carboxamidophenyl]-6-(2-t-butyloxycarbonylhydrazino)-pyridazine was treated with an equimolar amount of dilute sulphuric acid to give the sulphate of the title compound.

EXAMPLE 19

Preparation of 3-[2-(3-Butylamino-2-hydroxypropoxy)-5-fluorophenyl]-6-hydrazinopyridazine.

By subjecting 4-fluorophenol to a series of reactions similar to those described in Examples 11(i), 1(i–ii) and 2(i–vi), the title compound may be prepared.

EXAMPLE 20

3-[2-(3-t-Butylamino-2-hydroxypropoxy)phenyl]-4-methyl-6-hydrazinopyridazine i. A freshly prepared solution of dimethylamine hydrochloride (14.5 g, 0.18 mole) in 37% aqueous formaldehyde solution (10.5 ml, 0.14 mole) was allowed to stand for 30 minutes. Acetic anhydride (80.4 g, 0.77 mole) was then added and the mixture stirred until a clear solution was obtained. To this solution was added 2-benzyloxypropiophenone (28.8 g, 0.12 mole), the stirred mixture was heated under reflux for 2 hours and then evaporated to dryness. Acetone (75 ml) was added to the residue, the mixture was heated under reflux for 5 minutes and the solvent evaporated off. The residue was treated with an excess of dilute sodium hydroxide solution, and the oil which separated was extracted into dichloromethane (3 × 50 ml). The extract was washed with water, dried and evaporated to give a crude mixture (31.4 g) of 1-(2-benzyloxyphenyl)-2-methyl-2-propen-1-one, and N,N-dimethyl 2-(2-benzyloxybenzoyl)-propylamine as an oil.

ii. The product from (i) above (23.2 g), potassium cyanide (9.13 g, 0.14 mole) and methanol (500 ml) was stirred and heated under reflux for 16 hours. The reaction mixture was then evaporated to dryness, and water and dichloromethane were added to the residue. Evaporation of the washed and dried organic extract gave crude 3-(2-benzyloxybenzoyl)-butyronitrile (20.3 g, 93%) as an oil.

iii. The crude nitrile from (ii) (20.3 g, 0.073 mole) in 5N hydrochloric acid (600 ml) was stirred and heated under reflux for 2 hours. Evaporation of the mixture gave an oily residue from which 3-(2-hydroxybenzoyl)-butyric acid was isolated by standard procedures as an oil (8.6 g) which was crystallised from cyclohexane (5.2 g, m.p. 95°–97°).

iv. 3-(2-Hydroxybenzoyl)butyric acid (4.0 g, 0.02 mole) was esterified in methanol in a similar manner to that described in Example 4(i) to give methyl 3-(2-hydroxybenzoyl)butyrate (4.0 g, 94%) as an oil.

v. Methyl 3-(2-hydroxybenzoyl)butyrate (3.5 g, 0.016 mole) was treated in the manner described in Example 4(ii) to give methyl 3-[2-(2,3-epoxypropoxy)benzoyl]butyrate as an oil (3.6 g, 86%).

vi. Methyl 3-[2-(2,3-epoxypropoxy)benzoyl]butyrate (2.4 g, 0.009 mole) was treated in the manner described in Example 4 (iii) to give methyl 3-[2-(3-t-butylamino-2-hydroxypropoxy)-benzoyl]butyrate as an oil (2.7 g, 88%).

vii. Methyl 3-[2-(3-t-butylamino-2-hydroxypropoxy)-benzoyl]-butyrate (2.2 g, 0.0065 mole) was cyclised in the manner described in Example 4(iv) and the product was purified by chromatography to give 6-[2-(3-t-butylamino-2-hydroxypropoxy)phenyl]-5-methyl-4,5-dihydro-3(2H)-pyridazinone.

viii. 6-[2-(3-t-Butylamino-2-hydroxypropoxy)phenyl]-5-methyl-4,5-dihydro-3(2H)-pyridazinone was employed in a sequence of reactions similar to those described in Example 2(ii–vi) to give the title compound.

EXAMPLE 21

6-Hydrazino-3-[2-(2-hydroxypropoxy-3-phenylethylaminopropoxy)-4-methoxyphenyl]pyridazine i. 6-Chloro-3-[2-(2,3-epoxypropoxy)-4-methoxyphenyl]pyridazine was reacted with phenylethylamine in boiling methanol for 30 minutes and the reaction mixture evaporated to give 6-chloro-3-[2-(2-hydroxy-3-phenethylaminopropoxy)-4-methoxyphenyl)]pyridazine.

ii. 6-Chloro-3-[2-(2-hydroxy-3-phenethylpropoxy)-4-methoxyphenyl]-pyridazine was reacted with hydrazine hydrate in a similar manner to that described in Example 7b(iii) to give the title compound.

EXAMPLE 22

4-(3-t-Butylamino-2-hydroxypropoxy)-3-(6-hydrazino-3-pyridazinyl)benzoic acid, methyl ester.

4-(3-t-Butylamino-2-hydroxypropoxy-3-[6-(2-t-butyloxycarbonylhydrazino)-3-pyridazinyl]benzoic acid (from Example 18(x)) is treated with hydrogen chloride in methanol to give the hydrochloride of the title compound. Substitution of ethanol and butanol for methanol in the above procedure gave the ethyl or butyl esters respectively.

EXAMPLE 23

Substitution of 3-(4-ethyl-2-hydroxybenzoyl)propionic acid or 3-(4-butyl-2-hydroxybenzoyl)propionic acid for 3-(2-hydroxy-4-methylbenzoyl)propionic acid in the general procedure of Example 3 gives 3-[2-(3-t-butylamino-2-hydroxypropoxy)-4-ethylphenyl]-6-hydrazinopyridazine and 3[4-butyl-2-(3-t-butylamino-2-hydroxypropoxy)phenyl]-6-hydrazinopyridazine respectively.

EXAMPLE 24

Alkylation of 3-chloro-6-(2,4-dihydroxyphenyl)-pyridazine with diethyl sulphate or butyl bromide under the general conditions of Example 7(a) (i) gives 3-chloro-6-(4-ethoxy-2-hydroxyphenyl)-pyridazine and 3-chloro-6-(4-butyloxy-2-hydroxyphenyl)pyridazine, respectively.

Substitution of 3-chloro-6-(4-ethoxy-2-hydroxyphenyl)pyridazine or 3-chloro-6-(4butyloxy-2-hydroxyphenyl)pyridazine for 3-chloro-6-(2-hydroxy-4-methoxyphenyl)pyridazine in the general procedure of Example 7(a) (ii)–(v) gives 6-[2-(3-t-butylamino-2-hydroxypropoxy)-4-ethoxyphenyl]-3-hydrazinopyridazine and 6-[4-butyloxy-2-(3-t-butylamino-2-hydroxypropoxy)-phenyl]-3-hydrazinopyridazine, respectively.

EXAMPLE 25

3-[4-But-3-enyloxy-2-(3-butylamino-2-hydroxypropoxy)phenyl]-6-hydrazinopyridazine i. 3-Chloro-6-(2,4-dihydroxyphenyl)pyridazine was reacted with but-3-enyl bromide under similar conditions to those described in Example 7a(i) to give 6-(4-but-3-enyloxy-2-hydroxyphenyl)-3-chloropyridazine.

ii. 6-(4-But-3-enyloxy-2-hydroxyphenyl)-3-chloropyridazine was employed in a series of reactions similar to those described in Example 7b (i-iii) to give the title compound.

EXAMPLE 26

3-[2-(3-t-Butylamino-3-hydroxypropoxy)-5-butyramidophenyl]-6-hydrazinopyridazine Addition of butyric anhydride to a stirred suspension of 6-[5-amino-2-(3-t-butylamino-2-hydroxypropoxy)phenyl]-3(2H)-pyridazinethione in an aqueous buffer solution at pH 5.5 gives 6-[2-(3-t-butylamino-2-hydroxypropoxy)-5-butyramidophenyl]-3(2H)pyridazinethione, which gives the title product when boiled with hydrazine hydrate in ethanol.

EXAMPLE 27

Treatment of methyl 3-[5-trifluoroacetylamino-2-(2-trifluoroacetoxy-3-N-trifluoroacetylisopropylaminopropoxy)benzoyl]propionate with ethyl iodide or butyl bromide under the general conditions of Example 15(iii) and subsequent hydrolysis gives 3-[5-ethylamino-2-(2-hydroxy-3-isopropylaminopropoxy)benzoyl]propionic acid and 3-[5-butylamino-2-(2-hydroxy-3-isopropylaminopropoxy)benzoyl]propionic acid, respectively.

Substitution of 3-[5-ethylamino-2-(2-hydroxy-3-isopropylaminopropoxy)benzoyl]propionic acid or 3-[5-butylamino-2-(2-hydroxy-3-isopropylaminopropoxy)benzoyl]propionic acid for 3-[2-(2-hydroxy-3-isopropylaminopropoxy)-5-(methylamino)benzoyl]propionic acid in the general procedure of Example 15 (iv-vi) leads to the production of 3-[5-ethylamino-2-(2-hydroxy-3-isopropylaminopropoxy)phenyl]-6-hydrazinopyridazine and 3-[5-butylamino-2-(2-hydroxy-3-isopropylaminopropoxy)phenyl]-6-hydrazinopyridazine, respectively.

EXAMPLE 28

Treatment of 6-[5-amino-2-(2-acetoxy-3-N-acetyl-t-butylaminopropoxy)phenyl]-3(2H)-pyridazinone with diethyl sulphate or butyl bromide and sodium acetate in aqueous ethanol gives 6-[2-(2-acetoxy-3-N-acetyl-t-butylaminopropoxy)-5-diethylaminophenyl]-3(2H)-pyridazinone and 6-[2-(2-acetoxy-3-N-acetyl-t-butylaminopropoxy)-5-dibutylaminophenyl]-3(2H)-pyridazinone respectively. When the latter two compounds are subjected to a series of reactions similar to those described in Example 2(iv-vi) 3-[2-(3-t-butylamino-2-hydroxypropoxy)-5-diethylaminophenyl]-6-hydrazinopyridazine and 3-[2-(3-t-butylamino-2-hydroxypropoxy)-5-dibutylaminophenyl]-6-hydrazinopyridazine are prepared.

EXAMPLE 29

| Ingredients | Amounts |
|---|---|
| 3-[2-(3-t-Butylamino-2-hydroxypropoxy)phenyl]-6-hydrazino-pyridazine hemisulphate | 75 mg |
| Sucrose | 40 mg |
| Starch | 15 mg |
| Talc | 3 mg |
| Stearic Acid | 1 mg |

The ingredients are screened, mixed and filled into a hard gelatin capsule.

EXAMPLE 30

| Ingredients | Amounts |
|---|---|
| 3-[2-(3-t-Butylamino-2-hydroxypropoxy)phenyl-6-hydrazino-pyridazine hemisulphate | 100 mg |
| Lactose | 50 mg |

The ingredients are screened, mixed and filled into a hard gelatin capsule.

What is claimed is:

1. A compound of the Formula:

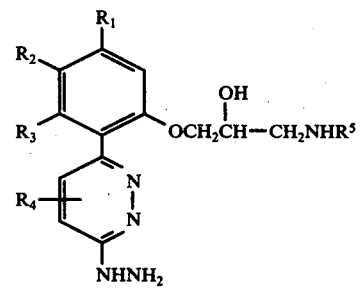

wherein two of the groups $R_1$, $R_2$ and $R_3$ are hydrogen and the third group is hydrogen, lower akyl, fluoro, chloro, bromo, trifluoromethyl, hydroxy, lower alkoxy, lower alkenyloxy, lower alkoxycarbonyl, cyano, —$CONH_2$, —$CH_2CONH_2$, nitro, amino, lower alkanoylamino, lower alkylamino or di(lower alkyl)amino; $R_4$ is hydrogen or methyl; $R^5$ is isopropyl, tertiary butyl or phenylethyl; or a pharmaceutically acceptable salt thereof.

2. A compound according to claim 1 wherein two of the groups $R_1$, $R_2$ and $R_3$ are hydrogen and the third group is hydrogen, methyl, fluoro, chloro, methoxy or cyano.

3. A compound according to claim 1 wherein $R_1$, $R_2$ and $R_3$ are all hydrogen.

4. A compound according to claim 1 wherein $R_3$ is hydrogen and either $R_1$ or $R_2$ is trifluoromethyl, allyloxy, -$CH_2CONH_2$ and acetamido.

5. A compound according to claim 4 wherein $R_3$ is hydrogen and either $R_1$ or $R_2$ is —$CH_2CONH_2$ or acetamido.

6. A compound according to claim 1 wherein $R_4$ is hydrogen.

7. A compound according to claim 1 wherein $R^5$ is isopropyl or tertiary butyl.

8. A compound according to claim 1, said compound being 3-[2-(3-t-butylamino-2-hydroxypropoxy)phenyl]-6-hydrazinopyridazine or a pharmaceutically acceptable salt thereof.

9. A compound according to claim 8, said compound being a salt of 3-[2-(3-t-butylamino-2-hydroxypropoxy)phenyl]-6-hydrazinopyridazine with sulphuric acid.

10. A compound according to claim 9, said compound being 3-[2-(3-t-burylamino-2-hydroxypropoxy)phenyl]-6-hydrazinopyridazine hemisulphate.

11. A compound according to claim 1, said compound being 3-[2-(3-t-butylamino-2-hydroxypropoxy)-4-methylphenyl]-6-hydrazinopyridazine or a pharmaceutically acceptable salt thereof.

12. A compound according to claim 1, said compound being 3-[2-(3-t-butylamino-2-hydroxypropoxy)-4-methoxylphenyl]-6-hydrazinopyridazine or a pharmaceutically acceptable salt thereof.

13. A compound according to claim 1, said compound being 3-[2-(3-t-butylamino-2-hydroxypropoxy)-6-fluorophenyl]-6-hydrazinopyridazine or a pharmaceutically acceptable salt thereof.

14. A compound according to claim 1, said compound being 3-[4-acetamido-2-(3-t-butylamino-2-hydroxypropoxy)phenyl]-6-hydrazinopyridazine or a pharmaceutically acceptable salt thereof.

15. A compound according to claim 1 in the S-absolute configuration.

16. A pharmaceutical composition to concomitantly inhibit β-adrenergic receptors and produce vasodilatation comprising in an effective amount to inhibit said receptors and produce vasodilatation a compound of claim 1 in combination with a pharmaceutically acceptable diluent or carrier.

17. A method of concomitantly inhibiting β-adrenergic receptors and producing vasodilatation which comprises administering a compound of claim 1 internally to an animal in need thereof in an amount sufficient to block said receptors and produce vasodilatation.

18. A method of treating hypertension which comprises administering a compound of claim 1 internally to an animal in need therof in an amount sufficient to alleviate said condition.

19. A method of treating angina pectoris which comprises administering a compound of claim 1 internally to an animal in need thereof in an amount sufficient to alleviate said condition.

20. A method of treating cardiac arrhythmia which comprises administering a compound of claim 1 internally to an animal in need thereof in an amount sufficient to alleviate said condition.

21. A compound according to claim 2 wherein $R^5$ is isopropyl or tertiary butyl.

22. A compound according to claim 21 wherein $R_4$ is hydrogen.

23. A compound according to claim 1, said compound being 3-hydrazino-6-[2-(2-hydroxy-3-isopropylaminopropoxy)-phenyl]pyridazine.

24. A compound according to claim 1, said compound being 3-[2-(3-t-butylamino-2-hydroxypropoxy)-5-fluorophenyl]-6-hydrazinopyridazine.

25. A compound according to claim 1, said compound being 3-[4-allyloxy-2-(3-t-butylamino-2-hydroxypropoxy)-phenyl]-6-hydrazinopyridazine.

* * * * *

UNITED STATES PATENT AND TRADEMARK OFFICE
CERTIFICATE OF CORRECTION

PATENT NO. : 4,053,601

DATED : October 11, 1977

INVENTOR(S) : William John Coates, Anthony Maitland Roe, Robert Antony Slater and Edwin Michael Taylor It is certified that error appears in the above–identified patent and that said Letters Patent are hereby corrected as shown below:

On the first page of the patent, in the left-hand column, in item [30] add the following:

January 2, 1975    United Kingdom..........20

Column 4, line 38, "Ser. No. 531,597, now U.S. Pat. No. 3,946,353." should read -- Ser. No. 531,957, now U.S. Pat. No. 3,931,177. -- .

Column 8, line 32, "produce" should read -- product -- .

Column 12, line 64, "by" should read -- be -- .

Column 27, line 15, "[2-(3-Butylamino-" should read -- [2-(3-t-Butylamino- -- .

Column 31, line 2, "burylamino" should read -- butylamino -- .

Signed and Sealed this

Twenty-eighth Day of March 1978

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,053,601
DATED : October 11, 1977
INVENTOR(S) : William John Coates, Anthony Maitland Roe, Robert Antony Slater and Edwin Michael Taylor It is certified that error appears in the above-identified patent and that said Letters Patent are hereby corrected as shown below:

Column 11, FORMULA 13, that portion of the structural formula reading

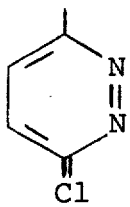  should read  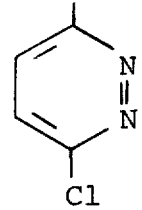

Column 12, FORMULA 16, that portion of the structural formula reading

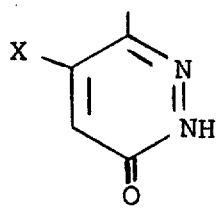  should read  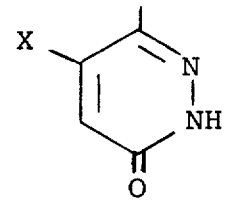

UNITED STATES PATENT AND TRADEMARK OFFICE
CERTIFICATE OF CORRECTION

PATENT NO. : 4,053,601

DATED : October 11, 1977

INVENTOR(S) : William John Coates, Anthony Maitland Roe, Robert Antony Slater and Edwin Michael Taylor It is certified that error appears in the above-identified patent and that said Letters Patent are hereby corrected as shown below:

Column 12, FORMULA 13, that portion of the structural formula reading

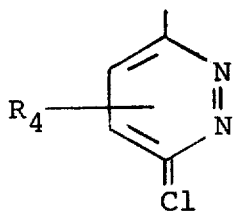   should read   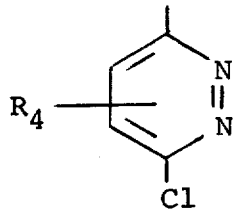

Signed and Sealed this

Sixteenth Day of January 1979

[SEAL]

Attest:

RUTH C. MASON
Attesting Officer

DONALD W. BANNER
Commissioner of Patents and Trademarks